United States Patent [19]

Takaku

[11] Patent Number: 5,134,228

[45] Date of Patent: Jul. 28, 1992

[54] NUCLEOSIDE-3'-PHOSPHITES FOR SYNTHESIS OF OLIGONUCLEOTIDES

[75] Inventor: Hiroshi Takaku, Funabashi, Japan

[73] Assignee: Central Glass Company, Limited, Ube, Japan

[21] Appl. No.: 412,990

[22] Filed: Sep. 26, 1989

[30] Foreign Application Priority Data

Sep. 29, 1988 [JP] Japan .................. 63-244748

[51] Int. Cl.⁵ .................. C07H 19/10; C07H 19/20
[52] U.S. Cl. ........................ 536/29; 536/27; 536/28
[58] Field of Search .................... 536/27-29

[56] References Cited

U.S. PATENT DOCUMENTS

| | | | |
|---|---|---|---|
| 3,188,309 | 6/1965 | Mukaiyama et al. | 536/27 |
| 3,188,310 | 6/1965 | Mukaiyama et al. | 536/27 |
| 4,415,732 | 11/1983 | Caruthers et al. | 536/27 |
| 4,668,777 | 5/1987 | Caruthers et al. | 536/27 |
| 4,672,110 | 6/1987 | Letsinger | 536/27 |
| 4,692,542 | 9/1987 | Tesser et al. | 558/184 |
| 4,725,677 | 2/1988 | Koster et al. | 536/27 |
| 4,789,737 | 12/1988 | Miyoshi et al. | 536/27 |

OTHER PUBLICATIONS

Tetrahedron Letters, vol. 22, No. 20, 1859 (1981), by S. L. Beaucage et al.
Nucleic Acids Res., vol. 14, 5399 (1986), by B. C. Froehler et al.
Chemical Abstracts, 101:38550W 1984 p. 519, Shreeve et al., (1984) Organometallics vol. 3, No. 7, pp. 1104-1107.
Watanabe et al., (1989), J. Am. Chem. Soc. vol. 111, pp. 3437-3439.
Denny et al., (1983), J. Org. Chem. vol. 48, pp. 2159-2164.
Takaku et al., (1988) Chemistry Letters, pp. 1675-1678.

Primary Examiner—John W. Rollins
Assistant Examiner—Gary L. Kunz
Attorney, Agent, or Firm—Fleit, Jacobson, Cohn, Price, Holman & Stern

[57] ABSTRACT

The invention provides novel phosphites represented by the general formula (I) and nucleoside-3'-phosphite derivatives represented by the general formula (III).

$$(RO)_3P \qquad (I)$$

wherein R is, for example, a fluoroalkyl group or a substituted phenyl group.

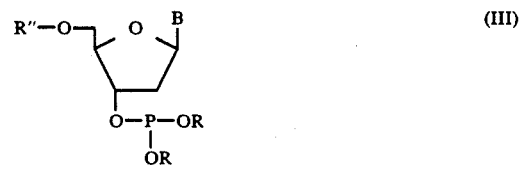

wherein R is the same as in (I), R" is a protecting group such as dimethoxytrityl group, and B represents a base, e.g. thymine.

A phosphite (I) is prepared by reacting an alcohol ROH with $PCl_3$ in the presence of a tertiary amine, and a nucleoside-3'-phosphite (III) is prepared by reacting a phosphite (I) with a nucleoside in a solvent in the presence of a tertiary amine. Phosphites (I) are very stable. Using a nucleoside-3'-phosphite (III) an oligonucleotide can be synthesized on a solid support by a simplified process.

6 Claims, No Drawings

NUCLEOSIDE-3'-PHOSPHITES FOR SYNTHESIS OF OLIGONUCLEOTIDES

BACKGROUND OF THE INVENTION

This invention relates to a group of novel phosphites and nucleoside-3'-phosphite derivatives useful for synthesis of oligonucleotides and to the synthesis of oligonucleotides using the novel nucleoside-3'-phosphites.

For the chemical synthesis of oligonucleotides the phosphoramidite approach is well known. However, this approach has disadvantages in several respects. In the synthesis of the phosphoramidite unit it is necessary to use chlorophosphine or a phosphitilating agent of bisamide type using an expensive azole. Both chlorophosphine and the obtained phosphoramidite unit are unstable. In the multi-step process an oxidation reaction is needed at each step. After the oligonucleotide synthesizing process there is the need of another reaction for eliminating the phosphate protecting group from the product.

The disadvantages of the phosphoramidite approach are obviated by the H-phosphonate approach. In this method the H-phosphonate unit is stable, and the reaction time is shorter than in the phosphoramidite approach. It is unnecesary to use a phosphate protecting group, and the process includes only one oxidation reaction which is carried out after completion of the condensation reaction.

However, there are still some problems about the H-phosphonate approach such as the unstableness of pivaloyl chloride used as a condensing agent in the condensation reaction, formation of hydrochlorides during the reaction and lack of a good phosphonylating agent for the phosphonate unit.

SUMMARY OF THE INVENTION

It is an object of the present invention to provide a novel phosphite which serves as a superior phosphitilating agent for nucleosides.

It is another object of the invention to provide nucleoside-3'-phosphite derivatives which use a phosphite of the invention and are useful and favorable for the synthesis of oligonucleotides by a solid-phase method.

It is still another object of the invention to provide a process of synthesizing an oligonucleotide using a nucleoside-3'-phosphite of the invention.

The present invention provides novel phosphites represented by the general formula (I):

$$(RO)_3P \tag{I}$$

wherein R represents $(CX_3)_nCX_m$, where each X is F, Cl, Br or H and is not necessarily similar to the others, n is 1, 2 or 3, and m is 0, 1 or 2, with proviso that n+m is 3, or 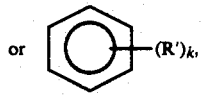

where R' is CN, $NO_2$, a halogen atom or a halogenated alkyl group and is not necessarily similar to the other(s), and k is 0 or an integer from 1 to 5.

In the general formula (I), R is a group high in acidity. Preferred examples of the group R are fluoroalkyl groups such as $(CF_3)_3C-$, $(CF_3)_2CH-$ and $CF_3CH_2-$, and other good examples are halogenated alkyl groups and phenol derivatives.

A phosphite of the general formula (I) is prepared by reacting an alcohol represented by the general formula (II) with phosphorus trichloride in the presence of a tertiary amine:

$$ROH \tag{II}$$

wherein R is as defined above with respect to the general formula (I).

The phosphites represented by the general formula (I) are useful as phosphitilating agents for various nucleosides. Compared with conventional phosphitilating agents, these phosphites have lower boiling points and hence can easily be obtained in refined form without decomposing during distillation under reduced pressure. These phosphites are high in stability and can be stored for a long time.

Furthermore, the invention provides nucleoside-3'-phosphite derivatives represented by the general formula (III):

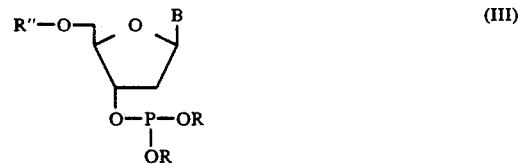

wherein R" is a protecting group, R is as defined above with respect to the general formula (I), and B represents a base.

As the protecting group R" in the formula (III), it is possible and preferable to employ dimethoxytrityl group which is prevailing as the protecting group in the conventional processes.

Representatives of the base B in the general formula (III) are $N^6,N^6$-dibenzoyladenine, $N^2$-isobutyrylguanine, $N^4$-benzoylcytosine and thymine.

A nucleoside-3'-phosphite of the general formula (III) is prepared by reacting a nucleoside represented by the general formula (IV) with a phosphite represented by the general formula (I) in a solvent in the presence of a tertiary amine:

wherein R" and B are as defined above with respect to the general formula (III).

The nucleoside-3'-phosphites of the general formula (III) are useful for the synthesis of oligonucleotides by the solid-phase method.

The present invention includes a process for the synthesis of an oligonucleotide, the process comprising the steps of (a) subjecting a nucleoside-3'-phosphite derivative represented by the general formula (III) to oligomerizing reaction on a solid support in the presence of a tertiary amine and treating the reaction product on the solid support with diluted trichloroacetic acid, (a') repeating the step (a) a plurality of times, (b) after the step (a') oxidizing the reaction product on the support by iodine, (c) detaching the reaction product from the support and (d) then eliminating the protecting group from the reaction product.

The principal merits of this process reside in that it suffices to carry out an oxidation reaction only once at the end of the oligomerizing process, that the product can easily be refined and that neither an expensive condensing agent nor an activator is needed.

DESCRIPTION OF THE PREFERRED EMBODIMENTS

To prepare a phosphite $(RO)_3P$ by reaction of phosphorus trichloride with an alcohol ROH in the presence of a tertiary amine, it is suitable to use 3 to 4 mols of the alcohol per mol of phosphorus trichloride. Preferred examples of the tertiary amine are triethylamine and pyridine. To obtain the aimed phosphite at high yield it is preferred to carry out the reaction by using 3 to 4 mols of a tertiary amine per mol of phosphorus trichloride in an organic solvent inactive to the reactants, such as ethyl ether, tetrahydrofuran, acetone or dichloromethane, at a temperature not very different from room temperature, viz. at 10°–35° C. Usually the reaction is completed in 2 to 5 hours.

A nucleoside-3'-phosphite represented by the general formula (III) is easily obtained by reacting a phosphite $(RO)_3P$ with a nucleoside represented by the general formula (IV) in an organic solvent inactive to the reactants in the presence of a tertiary amine. It is suitable to use 1 to 3 mols of the phosphite and 1 to 3 mols of the tertiary amine per mol of the nucleoside. The reaction smoothly proceeds at room temperature, and a suitable range of the reaction temperature is from 5° to 35° C. Examples of useful solvents are dichloromethane, ethyl ether, tetrahydrofuran, acetone, dioxane and acetonitrile. Examples of useful tertiary amines are pyridine, triethylamine, dimethylaminopyridine and N-methylimidazole. Usually the reaction is completed in less than 15 min. The aimed nucleoside-3'-phosphite of 99% purity (by $^{31}$P-NMR analysis) can efficiently be obtained by washing the reaction liquid with phosphoric acid buffer liquid (pH 7.0) several times, then concentrating the liquid, washing the residual oil-like liquid with n-hexane and concentrating the washed liquid under reduced pressure.

Using a nucleoside-3'-phosphite of the general formula (III), an oligonucleotide can be synthesized by the solid-phase synthesis method. Usually the synthesis is carried out in the following manner.

A selected nucleoside is fixed to a solid support selected from commercial products such as, for example, cross-linked polystyrene, silica gel and porous glass. Then the solid support is packed in a reaction column, treated with trichloroacetic acid and washed with dichloromethane and acetonitrile. After these preparatory operations a phosphite derivative of the general formula (III) and a tertiary amine such as N-methylimidazole or dimethylaminopyridine, which is employed as an activator, are introduced into the reaction column together with a suitable solvent such as acetonitrile. The reaction is completed in several minutes. After the reaction the column is washed with acetonitrile and dichloromethane and then treated with trichloroacetic acid for the purpose of eliminating the protecting group such as dimethoxytrityl group. These operations are repeated to carry out condensation reaction using phosphite derivatives having desired bases until an aimed base sequence is formed. After that an oxidation treatment is made. Usually iodine is used as the oxidizing agent, and it is suitable to use 0.1M solution of iodine in a mixture of tetrahydrofuran, pyridine and water. The oxidation reaction is completed in less than 0.5 hr. Next, the column is treated with concentrated aqueous ammonia to detach the reaction product from the solid support. After separating the solid support by filtration, the filtrate is concentrated and treated with, for example, acetic acid for the purpose of deprotection of the terminal. The resultant liquid is concentrated and washed with, for example, water and ether, and finally the oligonucleotide is separated and refined by high speed liquid chromatography. At every reaction step of this process the yield of the aimed product reaches 95% or above.

EXAMPLE 1

A solution of 35 ml (330 mM) of 1,1,1,3,3,3-hexafluoro-2-propyl alcohol and 46 ml (330 mM) of triethylamine in 120 ml of ethyl ether was added to a solution of 8.7 ml (100 mM) of phosphorus trichloride in 10 ml of ethyl ether, and the mixed liquid was maintained at room temperature for 3 hr to accomplish the reaction between phosphorus trichloride and the alcohol. After that the reaction liquid was filtered to remove hydrochlorides. The filtrate was concentrated, and the residue was distilled under reduced pressure to obtain a distillate distillate at 38°–40° C./10 mmHg. This distillate was confirmed to be tris(1,1,1,3,3,3-hexafluoro-2-propyl)phosphite and amounted to 43 g (80% yield).

$^{31}$P-NMR (CDCl$_3$): 141.0 ppm
$^1$H-NMR (CDCl$_3$): 5.3–4.4 (m, 3H, CH)

EXAMPLE 2

First 5.00 g (9.18 mM) of 5'-O-dimethoxytritylthymidine was dissolved in 43 ml of dichloromethane, and to this solution 2.22 ml (27.54 mM) of pyridine and 8.31 ml (27.5 mM) of tris(1,1,1,3,3,3-hexafluoro-2-propyly)-phosphite were added. The resultant mixture was stirred at room temperature for 15 min to complete the reaction between the phosphite and the nucleoside. After that the reaction liquid was washed with phosphoric acid buffer liquid (pH 7.0) until complete removal of the excess phosphitilating agent, and the remaining organic phase was dried by sodium sulfate and then concentrated. The residue was washed with n-hexane and further concentrated under reduced pressure. As the result 7.18 g of 5'-O-dimethoxytritylthymidine-3'-O-di(1,1,1,3,3,3-hexafluoro-2-propyl)phosphite was obtained. The yield was 91%.

$^{31}$P-NMR (CDCl$_3$, 85% H$_3$PO$_4$): 140.1 ppm

EXAMPLES 3-5

The process of Example 2 was repeated except that, in place of the nucleoside used in Example 2, 5'-O-dimethoxytrityl-N$^2$-isobutyrylguanosine, 5'-O-dimethoxytrityl-N$^4$-benzoylcytidine and 5'-O-dimethoxytrityl-N$^6$,N$^6$-dibenzoyladenosine were used in Examples 3, 4 and 5, respectively. The products were as follows.

EXAMPLE 3

5'-O-dimethoxytrityl-N$^2$-isobutyrylguanosine-3'-O-di(1,1,1,3,3,3-hexafluoro-2-propyl)phosphite (91% yield).

$^{31}$P-NMR (CDCl$_3$, 85% H$_3$PO$_4$): 141.1 ppm

EXAMPLE 4

5'-O-dimethoxytrityl-$N^4$-benzoylcytidine-3'-O-di(1,1,1,3,3,3-hexafluoro-2-propyl)phosphite (89% yield).

$^{31}$P-NMR (CDCl$_3$, 85% H$_3$PO$_4$): 140.2 ppm

EXAMPLE 5

5'-O-dimethoxytrityl-$N^6$,$N^6$-dibenzoyladenosine-3'-O-di(1,1,1,3,3,3-hexafluoro-2-propyl)phosphite (92% yield).

$^{31}$P-NMR (CDCl$_3$, 85% H$_3$PO$_4$): 141.2 ppm

EXAMPLE 6

A solid support of CPG carrying DMTrT nucleoside (DMTr represents dimethoxytrityl group, and T represents thymine) was packed in a glass tube column. The support carried 47 μM/g of DMTrT nucleoside, and 75 mg of the support was used so that the quantity of DMTrT nucleoside in the column was 3.52 μM. The solid support in the glass tube was first treated with 3% solution of trichloroacetic acid in dichloromethane for removal of dimethoxytrityl group. Then the column was well washed with dichloromethane and acetonitrile.

Separately, a solution was prepared by dissolving 68.7 mg (70.4 μM) of 5'-O-dimethoxytritylthymidine-3'-O-di(1,1,1,3,3,3-hexafluoro-2-propyl)phosphite (the product of Example 2) in 200 μl of acetonitrile. To this solution 25 μl (352 μM) of N-methylimidazole was added, and immediately the solution was introduced into the glass tube column of the solid support to carry out oligomerizing reaction of the nucleoside-3'-phosphite. After the lapse of 2 min the column was washed with acetonitrile and dichloromethane and then treated with 3% solution of trichloroacetic acid in dichloromethane for removal of dimethoxytrityl group. By repeating these operations aimed d-(Tp)$_{14}$T was formed. Finally the column was treated with 0.1M iodine solution (tetrahydrofuran/pyridine/water: 43/3/3 by volume) for 0.5 hr, followed by washing with dichloromethane.

After that the solid support was treated with concentrated ammonia solution for detachment of the reaction product from the support. The resultant slurry was filtered, and the filtrate was concentrated and treated with 80% acetic acid for 10 min. Then the mixed liquid was concentrated under reduced pressure to completely remove acetic acid, and the residue was dissolved in a small quantity of water and repeatedly washed with ether. From the washed aqueous solution the reaction product was separated and refined by HPLC, using TSK gel DEAE-2SW to obtain refined d-(Tp)$_{14}$T.

At every step of the above process the yield of the aimed substance was more than 95%.

What is claimed is:

1. A nucleoside-3'-phosphite derivative represented by the formula (III):

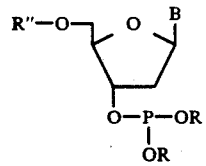

wherein R'' is a dimethoxytrityl group, B represents a base selected from the group consisting of $N^6$,$N^6$-dibenzoyladenine, $N^2$-isobutyryl-guanine, $N^4$-benzoylcytosine and thymine and R represents (CF$_3$)$_2$CH.

2. A process of synthesizing an oligonucleotide by using a nucleoside-3'-phosphite derivative according to claim 1, the process comprising the steps of:
   (a) subjecting said nucleoside-3'-phosphite derivative in the form of solution to oligomerizing reaction on a solid support which carries thereon a nucleoside in the presence of a tertiary amine and treating the reaction product on the solid support with diluted trichloroacetic acid to thereby remove a dimethoxytrityl group from the reaction product;
   (a') repeating the step (a) a plurality of times;
   (b) after the step (a') oxidizing the reaction product on the solid support by iodine in the form of solution;
   (c) detaching the oxidized reaction product from the solid support; and
   (d) eliminating the protecting group from the reaction product recovered by the step (c).

3. The process according to claim 2, wherein the steps (a), (a') and (b) are performed at room temperature.

4. The process according to claim 3, wherein the molar ratio of said nucleoside-3'-phosphite derivative to said nucleoside on said solid support is about 20:1, the molar ratio of said tertiary amine to said nucleoside-3'-phosphite derivative being about 5:1.

5. A process according to claim 4, wherein said tertiary amine is selected from the group consisting of N-methylimidazole and dimethylaminopyridine.

6. A process according to claim 5, wherein the step (c) is performed by treating said oxidized reaction product with concentrated aqueous ammonia.

* * * * *